(12) United States Patent
Katz et al.

(10) Patent No.: US 11,219,488 B2
(45) Date of Patent: Jan. 11, 2022

(54) DETERMINING CATHETER TOUCH LOCATION USING FORCE-VECTOR INFORMATION

(71) Applicant: BIOSENSE WEBSTER (ISRAEL) LTD., Yokneam (IL)

(72) Inventors: Natan Sharon Katz, Atlit (IL); Lior Zar, Poria Illit (IL); Benjamin Cohen, Haifa (IL); Israel Zilberman, Yokneam (IL); Ronen Krupnik, Karmiel (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 356 days.

(21) Appl. No.: 15/962,395

(22) Filed: Apr. 25, 2018

(65) Prior Publication Data
US 2019/0328459 A1 Oct. 31, 2019

(51) Int. Cl.
*A61B 34/20* (2016.01)
*A61B 5/06* (2006.01)
*A61B 5/00* (2006.01)

(52) U.S. Cl.
CPC .............. *A61B 34/20* (2016.02); *A61B 5/062* (2013.01); *A61B 5/065* (2013.01); *A61B 5/6843* (2013.01);
(Continued)

(58) Field of Classification Search
CPC ......... A61B 34/20; A61B 5/062; A61B 5/065; A61B 5/6843; A61B 2034/2051;
(Continued)

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

| WO | WO 96/05768 A1 | 2/1996 |
| WO | WO2014058838 A1 | 4/2014 |

(Continued)

OTHER PUBLICATIONS

European Search Report for corresponding EPA No. 19170915.3 dated Aug. 5, 2019.

*Primary Examiner* — Christopher Koharski
*Assistant Examiner* — Kaitlyn E Selmer
(74) *Attorney, Agent, or Firm* — Dergosits & Noah LLP; Todd A. Noah

(57) ABSTRACT

A system includes an electrical interface for communicating with a probe, and a processor. The electrical interface is configured to be inserted into a heart of a patient. The processor is configured to (A) receive from the probe, via the electrical interface, (i) position-signals indicative of a position of a distal tip of the probe in the heart, (ii) a contact-force indication indicative of a contact force exerted on the distal tip, and (iii) an electrophysiological (EP) measurement acquired by the distal tip at the position, (B) calculate a contact-force vector based on the contact-force indication received from the distal tip, and (C) based on the position-signals and on the contact-force vector, estimate a location, on an electro-anatomical map of the heart, at which the distal tip touches tissue, and to update the electro-anatomical map with the EP measurement, associated with the estimated location.

6 Claims, 3 Drawing Sheets

(52) U.S. Cl.
CPC .............. *A61B 2034/2051* (2016.02); *A61B 2034/2072* (2016.02)

(58) Field of Classification Search
CPC .......... A61B 2034/2072; A61B 5/6852; A61B 5/6869; A61B 5/6885; A61B 18/02; A61B 18/04; A61B 5/06; A61B 18/12; A61B 18/1492; A61B 2018/00351; A61B 2018/00357; A61B 2018/00702
See application file for complete search history.

(56) References Cited

U.S. PATENT DOCUMENTS

| | | | |
|---|---|---|---|
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 8,357,152 B2* | 1/2013 | Govari ............... | A61N 1/056 606/41 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2011/0125150 A1 | 5/2011 | Deno et al. | |
| 2011/0160570 A1* | 6/2011 | Kariv ............... | A61B 8/5276 600/424 |
| 2011/0184406 A1* | 7/2011 | Selkee ............... | A61B 5/6885 606/41 |
| 2011/0270046 A1* | 11/2011 | Paul ............... | A61M 25/0068 600/300 |
| 2011/0307207 A1 | 12/2011 | Govari et al. | |
| 2012/0041295 A1* | 2/2012 | Schultz ............... | A61B 5/6852 600/381 |
| 2012/0184863 A1* | 7/2012 | Harlev ............... | G16H 15/00 600/509 |
| 2014/0163376 A1* | 6/2014 | Caluser ............... | A61B 8/4254 600/443 |
| 2014/0364848 A1* | 12/2014 | Heimbecher ........ | A61B 5/6885 606/41 |
| 2016/0095653 A1* | 4/2016 | Lambert ............... | A61B 18/082 606/41 |
| 2016/0184032 A1 | 6/2016 | Romo et al. | |
| 2016/0278852 A1* | 9/2016 | Sliwa ............... | A61B 18/1492 |
| 2017/0065353 A1* | 3/2017 | Ludwin ............... | A61B 5/063 |
| 2017/0172457 A1* | 6/2017 | Govari ............... | A61B 5/066 |
| 2017/0245914 A1* | 8/2017 | Hauck ............... | A61B 5/0053 |
| 2017/0319279 A1* | 11/2017 | Fish ............... | A61B 18/12 |

FOREIGN PATENT DOCUMENTS

| | | |
|---|---|---|
| WO | WO2017197114 A1 | 11/2017 |
| WO | WO2018071490 A1 | 4/2018 |

* cited by examiner

DETERMINING CATHETER TOUCH LOCATION USING FORCE-VECTOR INFORMATION

FIELD OF THE INVENTION

The present invention relates generally to electro-anatomical mapping, and particularly to cardiac electro-anatomical mapping.

BACKGROUND OF THE INVENTION

Various techniques have been suggested for verifying catheter contact with cardiac tissue. For example, U.S. Pat. No. 8,357,152 describes a medical probe having a distal end for insertion into a body cavity of a patient, and a distal tip, which is disposed at the distal end of the probe and is configured to be brought into contact with tissue in the body cavity. A resilient member couples the distal tip to the distal end of the probe and is configured to deform in response to pressure exerted on the distal tip when the distal tip engages the tissue. A position sensor within the probe senses a position of the distal tip relative to the distal end of the probe, which changes in response to deformation of the resilient member. In some embodiments, signals provided by the position sensor in the probe are indicative of both the position of the distal end of the catheter and of force exerted on the distal tip.

As another example, U.S. Patent Application Publication 2011/0125150 describes a system and method for assessing effective delivery of ablation therapy to a tissue in a body. A three-dimensional anatomical map of the tissue is generated and displayed with the map defining a corresponding volume. An index is generated corresponding to a location within the volume with the index indicative of a state of ablation therapy at the location. The index may be derived from one or more factors such as the duration an ablation electrode is present at the location, the amount of energy provided, the degree of electrical coupling between an ablation electrode and the tissue at the location and temperature. In an embodiment, the orientation of an ablation electrode relative to tissue could be measured by a force vector sensor fitted on the catheter or through impedance measurements.

SUMMARY OF THE INVENTION

An embodiment of the present invention provides a system, including an electrical interface for communicating with a probe, and a processor. The electrical interface is configured to be inserted into a heart of a patient. The processor is configured to receive from the probe, via the electrical interface, (i) position-signals indicative of a position of a distal tip of the probe in the heart, (ii) a contact-force indication indicative of a contact force exerted on the distal tip, and (iii) an electrophysiological (EP) measurement acquired by the distal tip at the position. The processor is further configured to calculate a contact-force vector based on the contact-force indication received from the distal tip. The processor is additionally configured to, based on the position-signals and on the contact-force vector, estimate a location, on an electro-anatomical map of the heart, at which the distal tip touches tissue, and to update the electro-anatomical map with the EP measurement, associated with the estimated location.

In some embodiments, the processor is configured to estimate the location by comparing a first location estimated based on the contact-force vector with one or more second locations estimated based on the position-signals, and selecting one of the first and second locations to serve as the estimated location.

In some embodiments, the position-signals are provided by a position sensor fitted in proximity to the distal tip, and wherein the processor is configured to calculate a distance between the first location and the position sensor and, if the calculated distance exceeds a predefined distance, select one of the second locations to serve as the estimated location.

In an embodiment, the processor is configured to select the first location to serve as the estimated location if the calculated distance does not exceed the predefined distance.

There is additionally provided, in accordance with an embodiment of the present invention a method, including communicating with a probe that is configured to be inserted into a heart of a patient, and receiving from the probe (i) position-signals indicative of a position of a distal tip of the probe in the heart (ii) a contact-force indication indicative of a contact force exerted on the distal tip, and (iii) an electrophysiological (EP) measurement acquired by the distal tip at the position. A contact-force vector is calculated based on the contact-force indication received from the distal tip. Based on the position-signals and on the contact-force vector, a location at which the distal tip touches tissue is estimated on an electro-anatomical map of the heart. The electro-anatomical map is updated with the EP measurement, associated with the estimated location.

The present invention will be more fully understood from the following detailed description of the embodiments thereof, taken together with the drawings in which:

DETAILED DESCRIPTION OF EMBODIMENTS

Overview

Figure 1:
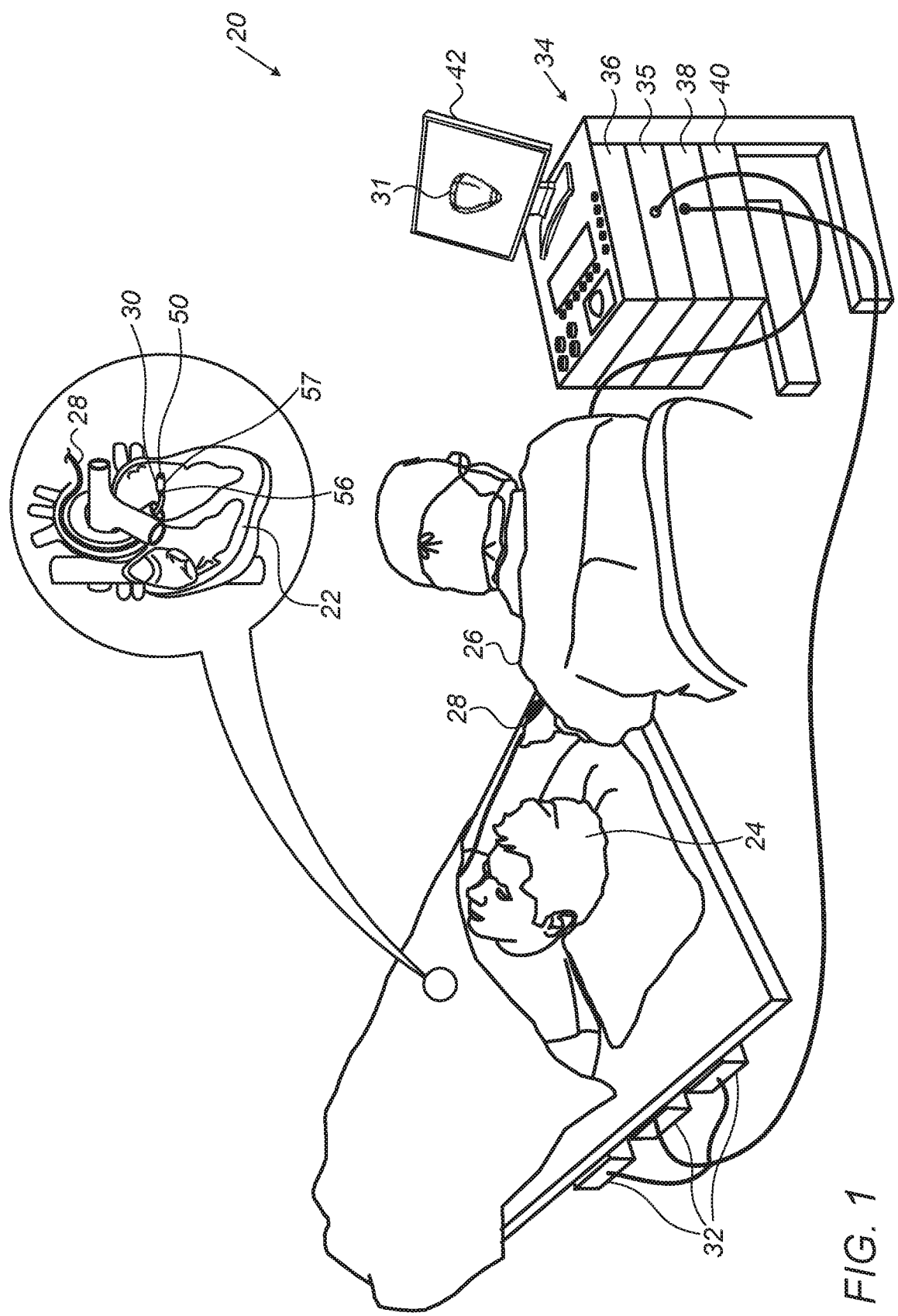
FIG. 1 is a schematic, pictorial illustration of a catheter-based cardiac location tracking and ablation system, in accordance with an embodiment of the present invention.

Mapping correctly a location where a catheter distal end is in contact (i.e., in touch) with tissue is important in cardiac diagnostic and therapy applications. For example, correct mapping of the location on the inner surface of a cardia chamber will enable a physician to acquire correct electro-anatomical data and as a result reach a correct diagnosis. Subsequently the physician can decide, for example, whether and how to perform an ablation at the location.

To measure the location of contact, the catheter may have a position sensor fitted at its distal end, usually in proximity to one or more distal electrodes. In the description hereinafter, for simplicity, a single distal electrode is described.

The distal electrode is used for acquiring electro-anatomical data (e.g., electrophysiological signals), such as an electrocardiogram at a touched location of the tissue, and might also be used for performing an ablation at the location, if necessary. A processor may determine the location where the distal electrode touches tissue as the closest point on an electro-anatomically mapped surface of cardiac tissue to the position measured by the position sensor.

In such determination process, a processor may utilize an electro-anatomical map, which has been already obtained, at least in part, by the catheter. The processor may project the position measured by the position sensor in numerous directions onto the map, and choose one or more closest intersection-points with mapped tissue surface as candidate touch locations of the electrode.

Practically, multiple, possibly contradicting candidate touch locations on the tissue surface may comply well with the position measured by the position sensor, within a certain tolerance. Thus, the determination process described above may produce wrong or inconclusive results. For example, a wrong result may occur if the distal end of the catheter is not oriented perpendicular to the surface of tissue, as explained below. As another example, when the tissue in the vicinity of the catheter distal end has a curving geometry, more than one location on the electro-anatomical map may be nearest to the position sensor, with no ability to distinguish the correct location that the distal electrode actually touches.

Embodiments of the present invention use a catheter having contact-force sensing capability, to measure the force exerted by tissue on the distal end (i.e., to measure a contact force vector). A processor uses the contact force vector information as an input, in addition to a position measurement by a position sensor, in determining the touched location. The direction of the force (named hereinafter 'force vector') gives additional information as to where, in relation to the distal end position, the touched location might be, as elaborated below.

Thus, the processor uses two criteria to determine the touched location: the closest point on mapped tissue to a measured position by a position sensor, and a location on the mapped tissue that the force vector indicates. In an embodiment, both candidate locations are quantified, to cover different scenarios, and a method is provided to determine which of the candidate touch locations is the correct one.

In many cases, a touch location determined based on contact force vector may be more accurate than a location determined using the position sensor. The typical cause would be that a force determined location directly indicates, in real-time, the touched location on tissue that induced the force. The correlation of a position with an anatomical map, on the other hand, may be less definitive, as was shown above.

In the description hereinafter, a location derived based on force vector is termed 'first location.' One or more nearest locations on a map derived based on projecting a position of a position-sensor are termed 'second locations.'

The disclosed technique can thus substantially improve the accuracy of an electro-anatomical map. By improving accuracy, the disclose technique can greatly improve the quality of diagnostics and of treatment decision making, the quality of an ablation treatment, if chosen, or alternatively the best outcome of another therapeutic approach.

System Description

FIG. 1 is a schematic, pictorial illustration of a catheter-based cardiac location tracking and ablation system 20, in accordance with an embodiment of the present invention. System 20 may be based, for example, on the CARTO™ system, produced by Biosense Webster Inc. (Irvine, Calif.). This system comprises an invasive probe in the form of a catheter 28 and a control console 34. In the embodiment described hereinbelow, it is assumed that catheter 28 is used in generation an electro-anatomical map of an endocardial tissue and optionally ablating locations over tissue, as is known in the art. Alternatively, the catheter may be used for other therapeutic and/or diagnostic purposes in the heart or in other body organs.

A physician 26, inserts catheter 28 through the vascular system of a patient 24 so that a distal end 30 of the catheter enters a chamber of the patient's heart 22. The physician advances the catheter so that a distal tip of distal end 30 engages endocardial tissue at a desired location or locations. The distal tip is covered, at least in part, by a distal electrode 50, wherein electrode 50 may be used for acquiring electro-anatomical data and optionally for radiofrequency (RF) ablation. A processor 36 receives measured electro-anatomical data and produces an electro-anatomical map 31 of a portion of heart 22 of patient 24, which is seen on a display 42. Processor 36 further stores electro-anatomical map 31 in a memory. Distal end 30 comprises a contact force sensor 57 to measure the force that tissue (i.e., an inner surface of the heart) exerts on the distal tip when the tip is in physical contact with cardiac tissue.

Catheter 28 is typically connected by a suitable connector at its proximal end to console 34. The console may comprise an RF generator 40, which supplies high-frequency electrical energy via the catheter in case of a need for ablating tissue in the heart at a location engaged by the distal tip. Alternatively, the catheter and system may be configured to perform ablation by other techniques that are known in the art, such as cryo-ablation.

Console 34 uses magnetic position sensing to determine position coordinates of distal end 30 inside heart 22. For this purpose, a driver circuit 38 in console 34 drives field generators 32 to generate magnetic fields within the body of patient 24. Typically, the field generators are placed below the patient's torso at known positions external to the patient. The generated magnetic fields penetrate a predefined working volume that contains heart 22. In response to these magnetic fields, a magnetic field position sensor 56 within distal end 30 of catheter 28 generates position-signals, which are indicative of the position of sensor 56 relative to a fixed frame of reference defined by field generators 32. Processor 36 receives the position-signals via wires (not shown in the figures) running through catheter 28 and electrical-interface circuits 35. Processor 36 processes the position-signals in order to determine the position coordinates of position-sensor 56 and to provide an indication of the location of electrode 50 in heart 22. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and electrical-interface circuits 35 for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 20, processor 36 drives display 42 to give physician 26 visual feedback regarding the position of distal end 30 in the patient's body, as well as status information and guidance regarding the procedure that is in progress.

Determining Catheter Touch Location Using Force Vector Information

Figure 2:
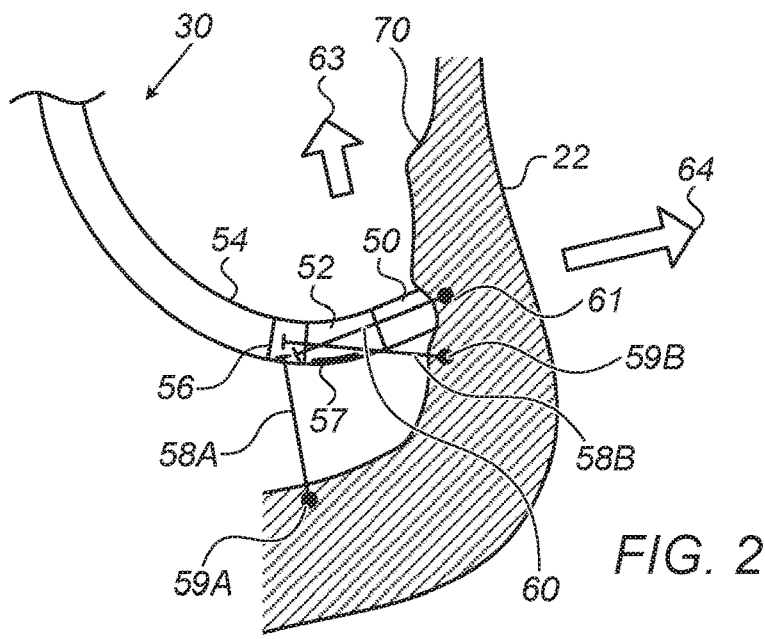
FIG. 2 is a schematic, side-view of a distal end of a catheter, showing details of the catheter distal end, in accordance with an embodiment of the present invention.

FIG. 2 is a schematic, side-view of distal end 30 of catheter 28, showing details of distal end 30, in accordance with an embodiment of the present invention. Distal end 30 comprises a flexible distal section 54, and a distal tip 52. Distal section 54 is flexible, to permit unimpeded bending and compression. Distal tip 52 is typically relatively rigid in comparison with the flexible distal section 54. As seen, distal tip 52 includes distal electrode 50.

A limited range of bending of flexible distal section 54 is allowed, in response to a mechanical force 63 exerted on distal tip 52 by the tissue. Contact force sensor 57 measures this force. Forces such as force 63 are encountered when distal tip 52 is pressed against the endocardium during, for example, electro-anatomical mapping and/or ablation procedures. The desired contact pressures for achieving good electrical contact between the distal tip and the endocardium during, for example, electro-anatomical mapping and/or ablation, are known. Thus, in response to the applied pressure, distal section 54 may be configured, for example, to permit sufficient bending, which results in lateral change of location of the distal tip by up to about the length of distal tip 52 and by corresponding angular deflection of distal tip 52 of up to about ninety degrees relative to flexible distal section 54.

As seen in FIG. 2, flexible distal section 54 comprises magnetic position sensor 56, which is positioned in proximity to distal tip 52. Processor 36 uses position sensor 56 in order to determine a position of electrode 50. In some embodiments, position sensor 56 may also serve as a contact force sensor that indicates a contact force exerted on distal tip 52. The position sensor provides the indication of contact force based on a signal indicative of an axial displacement and an orientation of the distal tip relative to the distal end, as described in detail in U.S. Pat. No. 8,357,152, whose disclosure is incorporated herein by reference. In such a case, position sensor 56 also acts as contact force sensor 57. Generally, any another type of pressure sensor may be fitted at distal section 54 or distal tip 52, to measure forces exerted on the distal tip 52. Such sensors may be, for example, strain sensors.

In some embodiments, processor 36 is configured to analyze the force exerted on distal tip 52, as sensed by contact force sensor 57, and determine a force vector 63 (i.e., force magnitude and direction). Based on force vector 63, processor 36 derives a force vector perpendicular 64. In general, two opposing vector perpendiculars exist, and processor 36 selects force vector perpendicular 64 that is approximately parallel to a direction defined from position sensor 56 to electrode 50, while ignoring the anti-parallel vector perpendicular.

As shown below, processor 36 uses force vector perpendicular 64 in determining a touched location candidate based on contact force, i.e., a first location 61. Such determination relies on the geometry that bent distal section 54 defines, being largely in a direction perpendicular to the force vector.

In an embodiment, a location on the electro-anatomical map that calculated force vector perpendicular 64 points at is a candidate touch location. The reason, as shown below, is that force vector perpendicular 64 generally points at the direction of the distal tip while the tip in contact with the tissue.

As noted above, using force vector perpendicular 64, and based on the known physical length of distal tip 52, processor 36 provides an estimation of first location 61 of electrode 50 relative to sensor 56. In particular, processor 36 calculates the length of force vector perpendicular 64, which is defined as the distance between (i) an estimated touched first location 61 on electro-anatomical map 31 that processor 36 determines perpendicular vector 64 to be aiming at, and (ii) position sensor 56. This length is named hereinafter Force Vector Derived Distance, 'FVDD'. As shown below, FVDD will serve to set criteria so as to accurately determine the location at which electrode 50 touches tissue.

The advantage of determining the touch location based on force vector is illustrated in the case exemplified by FIG. 2. As can be seen in the figure, if the calculation were to be based only projecting the position of position sensor 56 on a map for finding candidate second locations on map that are nearest to sensor 56, two candidate locations of electrode 50 were to be available, second locations 59A and 59B. Yet, as further seen, due to the curving of a cardiac surface 70 of heart 22, second locations 59A and 59B in fact differ significantly. Furthermore, in the example brought by FIG. 2, the sharp curvature of the wall of tissue 70, may cause a wrong location (second location 59A) to be actually be closer to position sensor 56. In other words, if distance 58A between position sensor 56 and second location 59A is even slightly smaller than distance 58B between position sensor 56 and second location 59B, second location 59A may be erroneously selected as the estimated touched location.

To avoid such error in touched location, processor 36 adds, as first step, a touch location candidate that is based on force vector perpendicular 64. The derivation of FVDD by processor 36 is provided herein step by step: (a) measure force vector 63 (b) derive a respective force vector perpendicular 64 (c) parallel move perpendicular force vector so as to originate from sensor 56 (d) elongate the perpendicular force vector to a point it crosses a tissue location on the electro-anatomical map, which in the exemplified case comes as first location 61, and (e) calculate the norm (length) of the elongated perpendicular force vector, which is the required FVDD.

As seen in FIG. 2, determined candidate second locations 59A and 59B, and first location 61, on cardiac surface 70 are all comparable in distance from sensor 56 (i.e., respective distances 58A, 58B and 60 are comparable). Yet, clearly in the exemplified case, location 59A is wrong, location 59B is more accurate and location 61 is the correct location of electrode 50. Such and other conflicting inputs on the electrode exact location may arise in various scenarios. In an embodiment, a method is disclosed, as explained below, which enables processor 36 to arrive at the correct decision, i.e., decide which of the three different locations is the correct one.

As seen in FIG. 2, distance 60 is approximately the physical length between the sensor 56 and the distal edge of electrode 50. In the description herein after that length is denoted by "L". Any force derived determination of the touched location distance from position sensor 56 should equal approximately L. This constraint stems from the fact that the distance between sensor 56 and the touched tissue is limited by the physical length of tip 52 which is approximately L. Some error e is reasonable to expect. For example, location accuracy up to an error e that equals 1 mm is considered good, where L is measured in millimeters, and where in many embodiments L may equal several millimeters. Thus, a criterion may specify that if distance FVDD is larger than a predefined distance L+e (in millimeters), FVDD>L+e, (i.e., FVDD exceeds the predefined distance L+e), then processor 36 will select a touched location based on correlating sensor 56 position with the anatomical map as explained above (i.e., select a second location by projecting sensor 56 position on a nearest location the map).

In the example brought by FIG. 2, force vector derived distance 60 FVDD maintains FVDD≤L+e (i.e., FVDD is within the predefined distance) so both second locations 59A and 59B and first location 61 are possible, in principle. In such a case processor 36 will select the location determined from force vector 63, i.e., first location 61.

In an embodiment, in case that a touch location based on the estimated position of the distal tip, and a touch location based on the contact-force vector are both possible, processor 36 will select as a rule, the touch location based on the contact-force vector. The reason for that rule is clear: force determined location 61, when make sense (i.e., when FVDD≅L) directly indicate in real-time to the touched location on tissue that induced the force. The correlation with an anatomical map in such case, on the other hand, is less definitive, as the analysis above demonstrated.

In an embodiment, if a distance of a determined location from sensor 56 is larger than a given distance (e.g., a given distance of 6 mm), processor 36 will not select a touched location based on correlating sensor 56 position with an anatomical map, since a location that distant indicates that tissue surface is not mapped completely, which may result in the processor determining an erroneous electrode position, if using the correlative indication. In another embodiment, L is assigned with a value that is based on empirical evidence and required accuracy, rather than being given a value of tip 52 length. If FVDD is above certain preset value (of, for example, 6 mm), then if FVDD>L+e, processor 36 will not select a touched location based on correlating sensor 56 position with an anatomical map, since a location that distant indicates that tissue surface isn't mapped completely, which may result in the processor determining an erroneous electrode position, if using the correlative indication.

The example side-view illustration of distal end 30 shown in FIG. 2 is chosen purely for the sake of conceptual clarity. Other distal tips may be used, which include two or more distal electrodes. Other types of distal ends may be used, such as a multi-ray (i.e., multi-tip) device. The distal device may alternatively be a spiral guide wire carrying electrodes. Thus, it is to be understood that FIG. 2 provides a simplified case, e.g., of a single tip, in order to present the concept as clearly and simply as possible, without loss of generality.

Figure 3A:
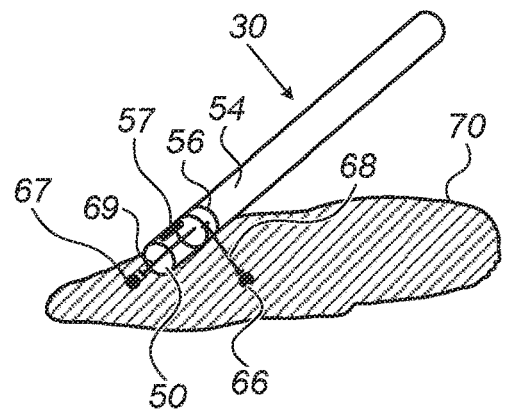
FIGS. 3A and 3B are schematic, pictorial illustrations of scenarios in which contact location between a catheter and tissue is determined, in accordance with an embodiment of the present invention.
Figure 3B:
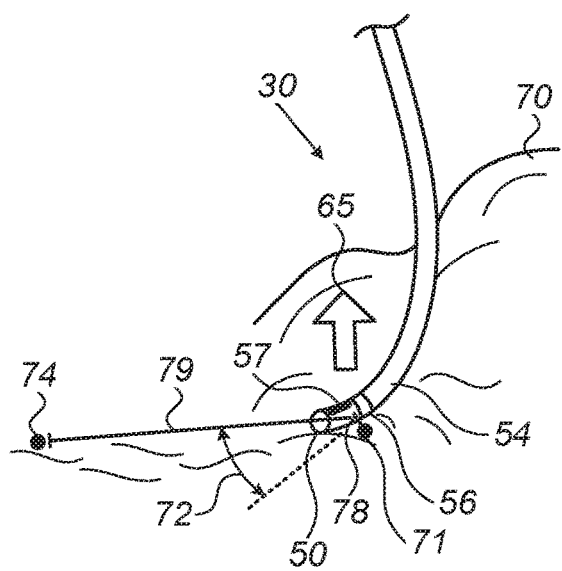

FIGS. 3A and 3B are schematic, pictorial illustrations of scenarios in which contact between a catheter and tissue is determined, in accordance with an embodiment of the present invention. The figures illustrate two scenarios:

FIG. 3A exemplifies a scenario in which cardiac surface 70 applies a weak but detectable force on distal electrode 50. In the example of FIG. 3A, catheter distal end 54 is nearly straight. As seen, an estimated second location 66, obtained from a correlation with a stored electro-anatomical map, and a first location 67, determined from force vector are located at similar distances from position sensor 56. Namely, distance 68 (FVDD) and distance 69 are comparable. As seen, FVDD≅L. Hence, according to the contact location determinization process discussed above, processor 36 will select correctly first location 67 that it determined from the force vector.

FIG. 3B exemplifies a scenario in which distal tip 52 is strongly bent, causing a large angular deflection 72, which results from a force vector 65 applied by cardiac surface 70 while being in firm contact with distal tip 52. As seen, a first location 74 determined from a force vector 65 is far away from electrode 50. On the other hand, a second location 71, determined from a correlation with stored electro-anatomical map 31, is located just near sensor 56. In other words, distance 79 is much larger than distance 78. As seen in FIG. 3B, distance 79 is much larger than then length L between sensor 56 and electrode 50, i.e., FVDD>>L, making the processor determination of second location 71 by the process described above clearly the correct one.

If no contact force is detected, distal electrode 50 is most likely not in touch with tissue at all. The disclosed technique provides a simple estimation of how far the distal tip may be from tissue. The estimation relies on the assumption that when no force is detected, the distal end is not bent. Therefore, the force vector perpendicular most likely points exactly parallel to the catheter tip direction. In this scenario, the location on the map where the force vector perpendicular aims at would serve as a determined location.

When distal tip 52 is in blood, clearly FVDD>L applies always and an enlarged error e may be used to practically determine an estimation of tip position based on the above considerations, where an error e may be on the order of the length of the tip itself. In an embodiment, the value of error e where such an estimation is valid, serves processor 36 to determine which of the candidate locations is more plausible, for example by comparing locations against using a criterion, for example, of e≤L for FVDD (i.e., by using a condition FVDD≤2L).

Figure 4:
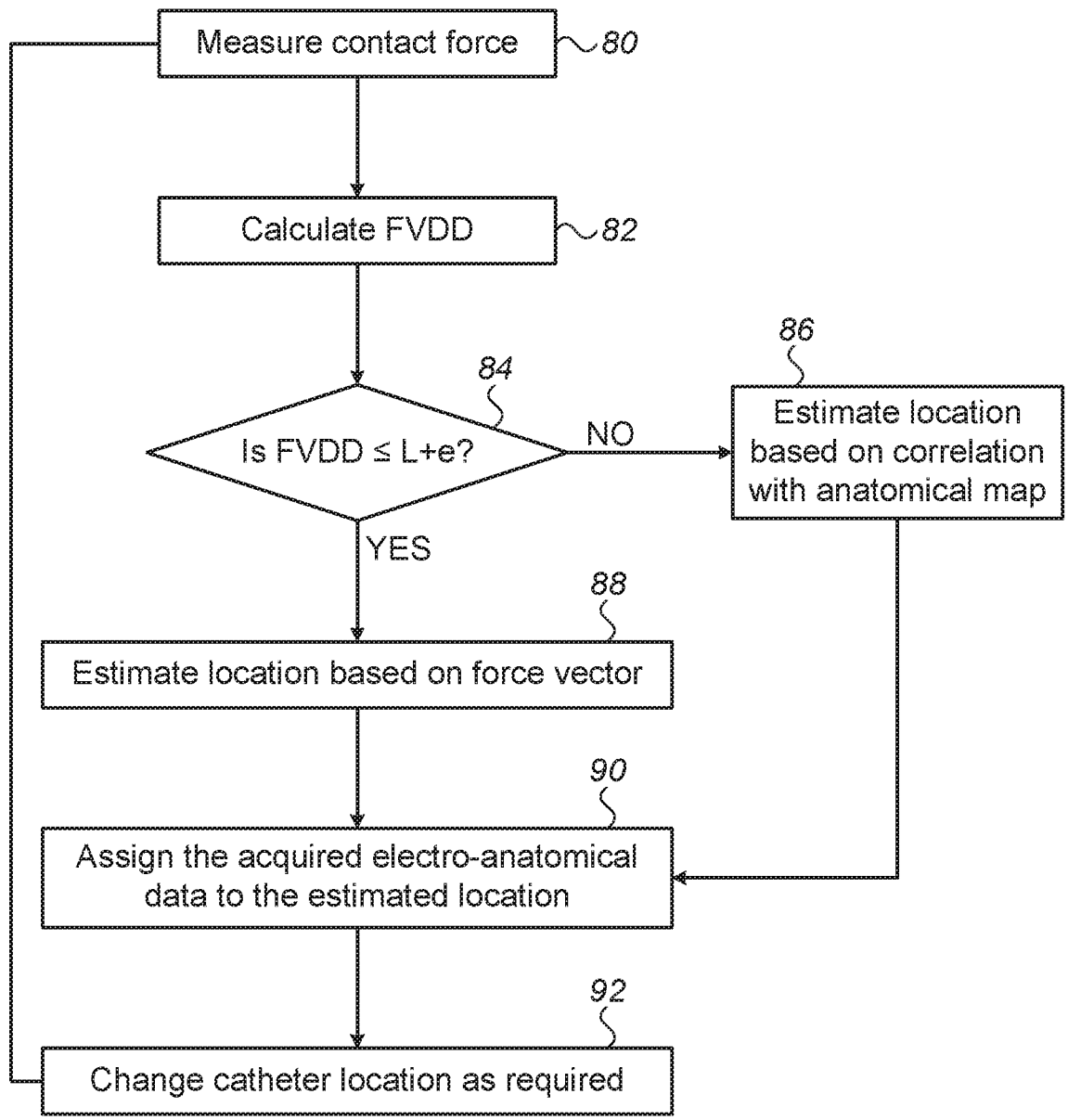
FIG. 4 is a flow-chart that schematically illustrates a method for determining a correct location of contact of a catheter distal end, in accordance with an embodiment of the present invention.

FIG. 4 is a flow-chart that schematically illustrates a method for determining a correct location of contact of distal tip 52 of catheter 28 with tissue, in accordance with an embodiment of the present invention. For simplicity of presentation, the process exemplified by FIG. 4 accounts for a scenario in which a contact force is always detected. The process may begin with contact force sensor 57 measuring the force exerted on distal tip 52 by cardiac surface 70, at a force measurement step 80.

Next, processor 36 calculates FVDD, at a calculation step 82. Processor 36 then compares FVDD with L+e, at a comparison step 84. If FVDD>L+e, then processor 36 has only a position measurement by sensor 56 to correlate with a nearest location on stored electro-anatomical map 31, so as to determine electrode 50 location, at a correlating step 86. If, on the other hand, at comparison step 84, FVDD≤L+e, then processor 36 determines the touch location, at a determination step 88, based on the calculated force vector (the force vector is calculated as an intermediate step in calculation FVDD at step 82).

Regardless of how the touch location has been estimated, processor 36 associates the acquired electro-anatomical data from electrode 50 with the estimated location, at a mapping step 90. The process may repeat by physician 26 changing catheter location as required, at a repositioning step 92, and jumps back to step 80.

The example flow chart shown in FIG. 4 is chosen purely for the sake of conceptual clarity. In alternative embodiments, additional steps may be added, such as ablation step, repeated measurements of contact force, and so on.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   electrical interface circuitry for communicating with a probe, the probe is configured to be inserted into a heart of a patient; and
   a processor, associated and communicating with the probe through the electrical interface circuitry, which is configured to:
      receive from the probe, via the electrical interface, (i) position-signals indicative of a position of a distal tip of the probe in the heart, (ii) a contact-force indication indicative of a contact force exerted on the distal tip, and (iii) an electrophysiological (EP) measurement acquired by the distal tip at the position;
      calculate a contact-force vector based on the contact-force indication received from the distal tip, wherein the contact force vector has a direction approximately parallel to a direction defined by the position signals;
      estimate a location on an electro-anatomical map of the heart at which the distal tip touches tissue, the location being estimated by comparing a first candidate touch location estimated based on the contact-force vector with one or more second candidate touch locations estimated based on the position-signals and selecting one of the first and second candidate touch locations; and
      update the electro-anatomical map with the EP measurement associated with the estimated location.

2. The system according to claim 1, wherein the position-signals are provided by a position sensor fitted in proximity to the distal tip, and wherein the processor is configured to calculate a distance between the first location and the position sensor and, if the calculated distance exceeds a predefined distance, select one of the second locations to serve as the estimated location.

3. The system according to claim 2, wherein the processor is configured to select the first location to serve as the estimated location if the calculated distance does not exceed the predefined distance.

4. A method, comprising:
   communicating with a probe that is configured to be inserted into a heart of a patient;
   receiving from the probe (i) position-signals indicative of a position of a distal tip of the probe in the heart (ii) a contact-force indication indicative of a contact force exerted on the distal tip, and (iii) an electrophysiological (EP) measurement acquired by the distal tip at the position;
   calculating a contact-force vector based on the contact-force indication received from the distal tip, wherein the contact force vector has a direction approximately parallel to a direction defined by the position signals;
   estimating a location on an electro-anatomical map of the heart at which the distal tip touches tissue, the location being estimated by comparing a first candidate touch location estimated based on the contact-force vector with one or more second candidate touch locations estimated based on the position-signals and selecting one of the first and second candidate touch locations; and
   updating the electro-anatomical map with the EP measurement associated with the estimated location.

5. The method according to claim 4, wherein the position-signal are provided by a position sensor fitted in proximity to the distal tip, and wherein estimating the location comprises calculating a distance between the first location and the position sensor and, if the calculated distance exceeds a predefined distance, selecting one of the second locations to serve as the estimated location.

6. The method according to claim 5, wherein estimating the location comprises selecting the first location to serve as the estimated location if the calculated distance does not exceed the predefined distance.

* * * * *